(12) United States Patent
Mitchnick

(10) Patent No.: US 10,166,146 B2
(45) Date of Patent: Jan. 1, 2019

(54) EAR MEDICATION DISPENSER WITH SENSOR

(71) Applicant: Mark Mitchnick, East Hampton, NY (US)

(72) Inventor: Mark Mitchnick, East Hampton, NY (US)

( * ) Notice: Subject to any disclaimer, the term of this patent is extended or adjusted under 35 U.S.C. 154(b) by 108 days.

(21) Appl. No.: 14/200,467

(22) Filed: Mar. 7, 2014

(65) Prior Publication Data

US 2014/0257171 A1 Sep. 11, 2014

Related U.S. Application Data

(60) Provisional application No. 61/774,973, filed on Mar. 8, 2013.

(51) Int. Cl.
*A61F 11/00* (2006.01)
*A61N 5/06* (2006.01)

(52) U.S. Cl.
CPC .............. *A61F 11/00* (2013.01); *A61N 5/062* (2013.01); *A61N 2005/0605* (2013.01)

(58) Field of Classification Search
CPC . A61B 1/227; A61B 2017/22062; A61B 5/01; A61B 5/0008; A61B 5/6817; A61B 2010/0019; A61B 2562/0271; A61B 5/0075; A61B 5/0086; A61B 5/14552; A61B 5/1491; A61B 5/6844; A61B 17/3468; A61B 17/3478; A61B 1/00082; A61B 1/015; A61B 1/018; A61B 1/043; A61B 1/2736; A61B 2017/306; A61B 2017/3425; A61B 2017/3441; A61B 5/1076; A61B 5/1077; A61B 5/1079; A61F 11/00; A61M 31/00; A61M 5/172; A61M 2202/0482; A61M 2205/6081; A61M 39/10; A61N 2005/0605; A61N 5/062; A61L 2300/404; A61J 15/0003; A61J 15/00; A61J 2200/76; A61J 2205/20
See application file for complete search history.

(56) References Cited

U.S. PATENT DOCUMENTS

| | | | |
|---|---|---|---|
| 2002/0161379 A1* | 10/2002 | Kaplan | A61F 11/002 606/109 |
| 2004/0102758 A1* | 5/2004 | Davila | A61B 17/0644 604/500 |
| 2006/0030837 A1* | 2/2006 | McKenna | A61F 11/00 604/890.1 |
| 2006/0095066 A1* | 5/2006 | Chang | A61B 34/20 606/199 |
| 2008/0318918 A1 | 12/2008 | Campbell et al. | 514/194 |
| 2009/0163890 A1* | 6/2009 | Clifford et al. | 604/514 |
| 2010/0198135 A1 | 8/2010 | Morriss et al. | 604/21 |
| 2011/0015489 A1 | 1/2011 | Raghuprasad et al. | 600/187 |
| 2011/0208161 A1* | 8/2011 | Ivri | A61F 11/00 604/514 |
| 2012/0327426 A1* | 12/2012 | Hart | A61B 1/00082 356/601 |

(Continued)

*Primary Examiner* — Brandy S Lee
(74) *Attorney, Agent, or Firm* — Licata & Tyrell P.C.

(57) ABSTRACT

A device for dispensing medication to the ear with a tympanic membrane sensor and medication dispenser which dispenses medication upon identification of the tympanic membrane by the sensor is provided. Also provided are methods for using the device to dispense medications to the ear.

19 Claims, 1 Drawing Sheet

(56) References Cited

U.S. PATENT DOCUMENTS

2013/0023818 A1* 1/2013 Rosenblum ........... A61F 11/002
  604/28
2013/0027515 A1* 1/2013 Vinther .............. A61B 1/00177
  348/44

* cited by examiner

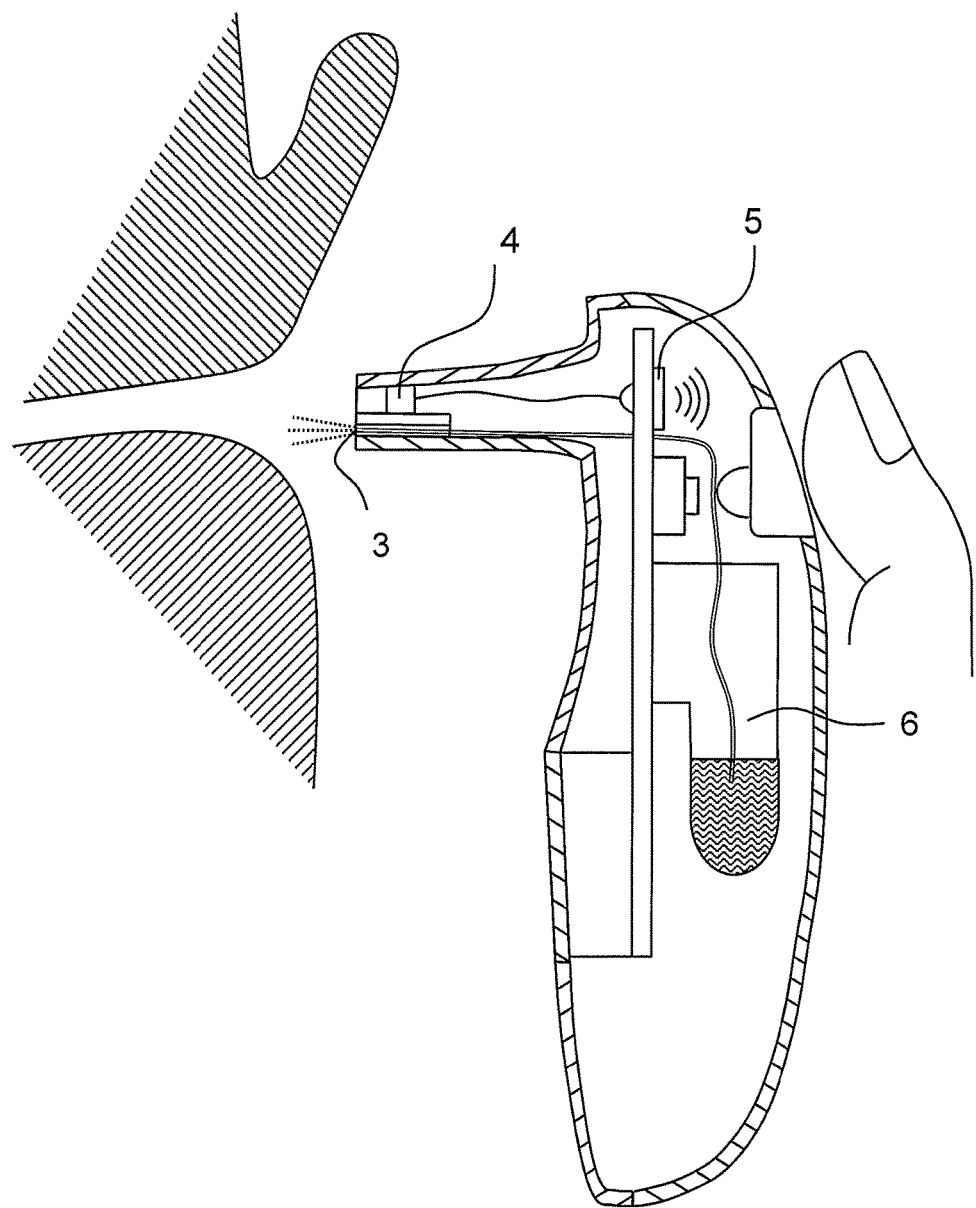

EAR MEDICATION DISPENSER WITH SENSOR

This patent application claims the benefit of priority from U.S. Provisional Application Ser. No. 61/774,973, filed Mar. 8, 2013, the content of which is herein incorporated by reference in its entirety.

FIELD OF THE INVENTION

Devices with a sensor capable of detecting the tympanic membrane for dispensing medications to the ear and methods for their use in dispensing medications to the ear are provided.

BACKGROUND

Ear pain is a very common complaint. Among the most common causes, especially in children, is otitis media, an inflammation of the middle ear without reference to etiology or pathogenesis. Otitis media can be classified into many variants on the basis of etiology, duration, symptomatology, and physical findings. Otitis media is the second most common disease of childhood, after upper respiratory infection (URI). Otitis media is also the most common cause for childhood visits to a physician's office. Annually, an estimated 16 million office visits are attributed to otitis media; this does not include visits to the emergency department.

Two current treatments for ear pain are systemic analgesics and local anesthetics.

Systemically administered drugs include, among others, non-steroidal anti-inflammatory drugs, acetaminophen and paracetamol. In severe cases, narcotics may be administered.

Local anesthetics include benzocaine, antipyrine, butamben, dibucaine, lidocaine, oxybuprocaine, pramoxine, proparacaine, proxymetacaine, and tetracaine. Presently, the only prescription product for in-home use in the United States to locally treat pain related to otitis media has two anesthetics, antipyrine and benzocaine. The two drugs are dissolved in glycerine and administered as drops. The formulation is well known to be messy and sticky.

Further, without the use of an otoscope, one cannot be assured that the medication is getting to the tympanic membrane quickly and in sufficient quantities.

Published U.S. Patent Application No. 2008/0318918 discloses a method for treating middle ear infections by transmembrane administration of a medicament-containing transmembrane carrier composition comprising a nonionic polymer surfactant to the tympanic membrane.

Published U.S. Patent Application No. 2010/0918135 discloses a system and method for use in iontophoretic anesthesia of the tympanic membrane inclusive of an earplug and electrode device.

Published U.S. Patent Application No. 2011/0015489 discloses an otoscope with an attachable ear wax removal device.

SUMMARY OF THE INVENTION

An aspect of the present invention relates to an ear medication delivery device which dispenses medication when the tympanic membrane is identified. The device comprises a tympanic membrane sensor and medication dispenser which dispenses medication upon identification of the tympanic membrane by the sensor. In one embodiment, the device dispenses the medication automatically upon sensing the tympanic membrane. In another embodiment, the device notifies the user that the tympanic membrane has been identified so that the user may initiate dispensing of the medication.

Another aspect of the present invention relates to a method for dispensing medication to the ear of a subject which comprises inserting into the ear canal of the subject an ear medication delivery device comprising a tympanic membrane sensor and medication dispenser which dispenses medication upon identification of the tympanic membrane by the sensor. In one embodiment, medication is dispensed from the medication dispenser automatically when the tympanic membrane is identified. In another embodiment, the device notifies the subject or another user of the device that the tympanic membrane has been identified so the subject or other user of the device can initiate dispensing of the medication.

BRIEF DESCRIPTION OF THE FIGURE

FIG. 1 is a diagram of an embodiment of an ear medication delivery device of the present invention.

DETAILED DESCRIPTION OF THE INVENTION

The present invention provides an ear medication delivery device and a method for its use in effectively delivering medication to the ear of a subject.

The ear medication delivery device of the present invention comprises a medication dispenser. In simplest form, the medication dispenser comprises at least one reservoir 6 for holding medication coupled to at least one medication dispensing head with orifice 3. The at least one medication dispensing head with orifice is connected to at least one reservoir and is preferably positioned at the tip of the portion of the ear medication delivery device. In this embodiment, the tip of the device is designed to fit comfortably within the ear canal so that upon insertion into the ear canal medication can be dispensed from the reservoir through the orifice of the medication dispensing head to an inner portion of the ear. The reservoir or reservoirs for holding of the medication can be positioned anywhere else on the device. In one embodiment, one or more reservoirs are in the device handle. In another embodiment, one or more reservoirs are positioned just behind the sensor. In one embodiment, the reservoir or reservoirs are fixed to the device. In this embodiment, the device is re-used by refilling the reservoir or reservoirs. In another embodiment, the reservoir or reservoirs are replaceable. In this embodiment, the reservoir or reservoirs may comprise a cartridge system designed to fit in the device which contains the medication or medications to be dispensed. The cartridge system may be designed to disposable after a single or finite number of uses. Alternatively, the cartridge may be washable and designed for re-use. In one embodiment, this system may further comprise a covering for the tip of the portion of the device inserted into the ear canal to minimize contamination. Various dispensers capable of delivery of one or more medications to the ear are known and can be adapted for use in the present invention. In one embodiment, a medication dispenser capable of delivery of one or more various medication formulations including but not limited to, powders, liquids, gels, dispersions and aerosols is used.

In one embodiment, the medication dispenser comprises multiple reservoirs which deliver multiple separate streams with at least one stream containing a medication. For example, the medication dispenser may be capable of delivering two separate streams at least one of which contains a medication. In this embodiment, the two streams may react providing benefit such as, but not limited to, a thicker formulation. In this embodiment, the device may comprise a single medication dispensing head with orifice connected to each of the reservoirs or may comprise separate medication dispensing heads and orifices connect to each reservoir.

In one embodiment, the ear medication delivery device may further comprise, at its tip, a light source that can be used to polymerize a medication containing stream if, for example, one of the streams contains a UV curable polymer.

The ear medication device further comprises a tympanic membrane sensor 4.

The tympanic membrane is a thin structure, well-perfused with blood, located at the internal end of the ear canal. Various tympanic membrane sensors are known and can be adapted for use in the ear medication dispensing device of the present invention. In one embodiment, the tympanic membrane sensor identifies the tympanic membrane by infrared detection. For example, tympanic thermometers are small hand-held devices with a temperature probe that is inserted into the subject's ear canal. A sensor at the end of the probe records the infrared radiation (IRR) that is emitted by the membrane as a result of its warmth and converts this into a temperature reading presented on a digital screen. The probe is protected by a disposable cover, which is changed between patients to prevent cross-infection. It has been suggested that tympanic thermometers give a more accurate representation of actual body temperature because the tympanic membrane lies closer to the temperature regulation center in the hypothalamus and shares the same artery (Van Staaij et al., 2003). The same sensor used in tympanic thermometers can be adapted for use in the present invention.

In one embodiment, the sensor is positioned at the tip of the portion of the ear medication delivery device designed to fit comfortably within the ear canal so that the tympanic membrane is easily detected upon insertion into the ear canal.

The ear medication delivery device further comprises a power source for the tympanic membrane sensor. In one embodiment, the power source is contained within the device. In another embodiment, the power source is external to the device. In one embodiment, the medication dispenser is also powered by the power source. In another embodiment, the dispenser is mechanical in nature and powered by the user. A nonlimiting example of this embodiment of dispenser is a trigger powered pump.

In one embodiment of the present invention, detection of the tympanic membrane by the sensor automatically initiates dispensing of the medication from the medication dispenser of the device.

In another embodiment, the device further comprises means 5 to alert the subject or the user of the device that the tympanic membrane has been detected so that the subject or user can initiate dispensing of the medication. Any means which emits a sound, light or vibration for instance can be used. In one embodiment, the device will provide an audible signal that the tympanic membrane is "in site" and that the drug has been delivered or that the user should initiate drug delivery through the use of a trigger or similar mechanism. In these embodiments, the alert means is powered by the same power source for the tympanic membrane sensor.

The ear medication delivery device of the present invention permits medication to be dispensed only when the tympanic membrane is identified, thus assuring that the medication reaches the tympanic membrane and site of action. Specifically, the device is placed into the ear canal and a sensor, similar to that used on tympanic thermometers or any other sufficient sensor lets the user know when the membrane is detected. Then the device automatically dispenses the medication. Alternatively, the device can alert the user or subject that the membrane has been located and the user or subject can then dispense the medication. The user can be alerted via any means which emits a sound, light or vibration for instance.

The ear medication delivery device of the present invention can be used to deliver various medications in various forms including, but not limited to powders, liquids, gels, dispersions and aerosols to the subject. In one embodiment, the device is used to deliver a medication can containing microparticles or nanoparticles. In one embodiment, the device is used to deliver an anesthetic and/or analgesic to the subject. In one embodiment, the device is used to deliver an antiviral, antimicrobial, steroidal or anti-inflammatory agent to the subject.

Accordingly, devices and methods of the present invention are useful in treating various conditions in a subject including, but not limited to, pain, infection, cancer and/or trauma.

In the method of the present invention, a medication is dispensed to the ear of a subject by inserting the device of the present invention into the subject's ear canal to a distance at which the tympanic membrane is identified by the sensor of the device. In one embodiment, medication is then dispensed from the medication dispenser automatically when the tympanic membrane is identified. In another embodiment, the device inserted into the subject's ear canal to a distance at which the tympanic membrane is identified by the sensor of the device further comprises a means to notify a user or the subject that the tympanic membrane has been identified. Once notified, the subject or user can initiate dispensing of the medication.

By "subject", as used herein, it is meant the individual being treated with the device and/or method of the present invention.

By "user", as used herein, it is meant the individual inserting the device into the ear canal of the subject. In one embodiment, the user may be the subject. In another embodiment, the user may be a health professional, a parent or guardian or another individual assisting the subject by inserting the device into the ear canal of the subject.

What is claimed is:

1. A device for dispensing medication to the tympanic membrane of the ear, said device comprising a tympanic membrane sensor which identifies the tympanic membrane by infrared detection, a means to notify a user when the sensor identifies the tympanic membrane, and a medication dispenser adapted to be inserted into the ear canal to a distance at which the tympanic membrane is identified by the tympanic membrane sensor, wherein medication is automatically dispensed from the medication dispenser at said distance.

2. The device of claim 1 wherein medication to be dispensed is in the form of a powder, liquid, gel, dispersion or aerosol.

3. The device of claim 1 wherein medication to be dispensed contains microparticles or nanoparticles.

4. The device of claim 1 wherein medication to be dispensed is an anesthetic and/or analgesic.

5. The device of claim 1 wherein medication to be dispensed is an antiviral, antimicrobial, steroidal, anti-inflammatory agent.

6. The device of claim 1 wherein medication to be dispensed treats pain, infection, cancer and/or trauma.

7. The device of claim 1 wherein the medication dispenser comprises at least one reservoir for holding medication coupled to a medication dispensing head with orifice.

8. The device of claim 7 wherein the medication dispensing head with orifice is positioned at a tip of a portion of the ear medication delivery device designed to fit comfortably within the ear canal so that upon insertion into the ear canal medication can be dispensed through the orifice of the medication dispensing head to an inner portion of the ear.

9. The device of claim 7 wherein the reservoir is in a handle of the device.

10. The device of claim 7 wherein the reservoir is fixed to the device.

11. The device of claim 7 wherein the reservoir is replaceable.

12. The device of claim 11 wherein the reservoir comprises a cartridge system designed to fit in the device which contains the medication to be dispensed.

13. The device of claim 12 wherein the cartridge system is disposable.

14. The device of claim 12 wherein the cartridge system is washable and/or re-usable.

15. The device of claim 7 wherein the medication dispenser comprises multiple reservoirs which deliver multiple separate streams with at least one stream containing a medication.

16. The device of claim 15 wherein the multiple reservoirs are connected to a single medication dispensing head with orifice.

17. The device of claim 15 wherein each of the multiple reservoirs are connected to separate medication dispensing heads and orifices.

18. The device of claim 1 further comprising a light source at its tip capable of curing an ultraviolet polymer.

19. A method of dispensing medication to the ear of a subject, said method comprising inserting the device of claim 1 into the subject's ear canal to a distance at which the tympanic membrane is identified by the sensor of the device; and dispensing the medication.

* * * * *